United States Patent
Blömer

(10) Patent No.: US 10,709,564 B2
(45) Date of Patent: Jul. 14, 2020

(54) KNEE ENDOPROSTHESIS FOR REPLACING AT LEAST PARTS OF THE KNEE JOINT

(71) Applicant: CeramTec GmbH, Plochingen (DE)

(72) Inventor: Wilhelm Blömer, Uhldingen-Mühlhofen (DE)

(73) Assignee: CeramTec GmbH, Plochingen (DE)

( * ) Notice: Subject to any disclaimer, the term of this patent is extended or adjusted under 35 U.S.C. 154(b) by 114 days.

(21) Appl. No.: 15/765,745

(22) PCT Filed: Oct. 4, 2016

(86) PCT No.: PCT/EP2016/073640
§ 371 (c)(1),
(2) Date: Apr. 4, 2018

(87) PCT Pub. No.: WO2017/060221
PCT Pub. Date: Apr. 13, 2017

(65) Prior Publication Data
US 2019/0091031 A1    Mar. 28, 2019

(30) Foreign Application Priority Data

Oct. 7, 2015    (DE) .................. 10 2015 219 344

(51) Int. Cl.
*A61F 2/38* (2006.01)
*A61L 27/10* (2006.01)
(Continued)

(52) U.S. Cl.
CPC ........ *A61F 2/3868* (2013.01); *A61F 2/30771* (2013.01); *A61F 2/38* (2013.01);
(Continued)

(58) Field of Classification Search
CPC .................. A61F 2/3868; A61F 2/389; A61F 2002/30649; A61F 2002/30934;
(Continued)

(56) References Cited

U.S. PATENT DOCUMENTS

| 6,013,013 A | 1/2000 | Wolf |
| 6,013,103 A | 1/2000 | Kaufman et al. |

(Continued)

FOREIGN PATENT DOCUMENTS

| CN | 1440262 A | 9/2003 |
| CN | 101317791 A | 12/2008 |

(Continued)

OTHER PUBLICATIONS

Office action in counterpart CN Appl. No. 201680058881.X dated May 20, 2019 with English translation and English translation of Search Report.

(Continued)

*Primary Examiner* — David H Willse
*Assistant Examiner* — Javier G Blanco
(74) *Attorney, Agent, or Firm* — Fitch, Even, Tabin & Flannery, LLP

(57) ABSTRACT

The invention relates to a knee endoprosthesis comprising a femoral component (1) which has two condylar surfaces (1a, 1b) for anchoring on the distal femur, comprising a tibial component (2) for anchoring on the proximal tibia, and comprising sliding surfaces between the two components (1, 2). It is proposed according to the invention that the entire femoral component (1), but at least its condylar surfaces (1a, 1b) are made of a solidly sintered ceramic for articulation with the tibial component (2), so that the knee endoprosthesis will have the least possible amount of abrasion with optimal reproduction of the anatomical and kinematic properties of the natural knee joint, in particular through suitable combinations of materials and by reducing the abrasion-generating surfaces. This is achieved by the fact that the tibial component (2) comprises a tibial baseplate (11) made of a solidly sintered ceramic which has a medial spherical bearing shell (7) on the upper face of the baseplate facing the (Continued)

Figure 1:
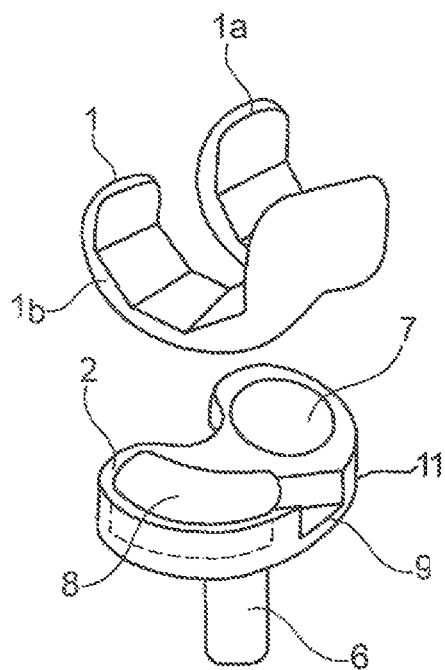

femoral component (1). The medial spherical bearing shell (7) is an integral component of the tibial baseplate (11) and is formed in one piece with it, and the articulation surface of the medial femur condyle (1*a*) is also designed to be spherical, and together with the medial spherical bearing shell (7), forms a congruent ball joint. Laterally adjacent to the medial spherical bearing shell (7), a bearing shell (8) which enables rotation of the femoral component (1) and is formed by multiple radii in the anterior-posterior direction is arranged non-congruently with the femoral condyle (1*b*) and is either formed integrally with the tibial baseplate (11) or is an inlay that is movable relative to the tibial baseplate (11).

5 Claims, 1 Drawing Sheet

(51) Int. Cl.
 *A61L 27/06* (2006.01)
 *A61F 2/30* (2006.01)
(52) U.S. Cl.
 CPC .............. *A61F 2/385* (2013.01); *A61F 2/389* (2013.01); *A61F 2/3845* (2013.01); *A61F 2/3859* (2013.01); *A61L 27/06* (2013.01); *A61L 27/10* (2013.01); *A61F 2002/3082* (2013.01); *A61F 2002/30133* (2013.01); *A61F 2002/30242* (2013.01); *A61F 2002/30649* (2013.01); *A61F 2002/30878* (2013.01); *A61F 2002/30934* (2013.01); *A61F 2002/30968* (2013.01); *A61F 2230/0071* (2013.01); *A61F 2310/00179* (2013.01); *A61L 2430/02* (2013.01)
(58) Field of Classification Search
 CPC .... A61F 2002/30242; A61F 2230/0071; A61F 2310/00179; A61F 2002/3082
 See application file for complete search history.

(56) References Cited

U.S. PATENT DOCUMENTS

| | | | | |
|---|---|---|---|---|
| 2006/0052875 | A1* | 3/2006 | Bernero | .................... A61F 2/38 623/20.33 |
| 2012/0136452 | A1* | 5/2012 | Richter | ................ A61F 2/3886 623/20.28 |

FOREIGN PATENT DOCUMENTS

| | | | | |
|---|---|---|---|---|
| CN | 102596108 A | 7/2012 | | |
| DE | 102011009616 A1 * | 8/2012 | .............. | A61F 2/38 |
| RU | 2057495 C1 | 4/1996 | | |
| RU | 2110972 C1 | 5/1998 | | |
| RU | 2145821 C1 | 2/2000 | | |

OTHER PUBLICATIONS

International Search Report for PCT/EP2016/073640, dated Dec. 6, 2016, and English Translation submitted herewith (5 pgs).
Office action in Russian Appln. No. 2018116595 dated Mar. 10, 2020.

* cited by examiner

KNEE ENDOPROSTHESIS FOR REPLACING AT LEAST PARTS OF THE KNEE JOINT

CROSS-REFERENCE TO RELATED APPLICATIONS

This application is a U.S. national phase application filed under 35 U.S.C. § 371 of International Application No. PCT/EP2016/073640, filed Oct. 4, 2016, designating the United States, which claims priority from German Patent Application No. 10 2015 219 344.6, filed Oct. 7, 2015, which are hereby incorporated herein by reference in their entirety.

The invention relates to a knee endoprosthesis comprising a femoral component having two condylar surfaces for anchoring on the distal femur and comprising a tibial component for anchoring on the proximal tibia and comprising sliding surfaces between these two components.

The invention relates in general to improvement of a knee endoprosthesis for replacing at least parts of the knee joint. A knee endoprosthesis for partial or total replacement of the knee joint typically consists of a femoral component for anchoring on the distal femur and a tibial component for anchoring on the proximal tibia, wherein the tibial component includes an insert or a meniscus component for articulation with the femur component.

U.S. Pat. No. 6,013,103 describes a knee endoprosthesis, in which the surface of the tibia part is designed to be flat and allows displacement of the meniscus part in this plane, such that the meniscus part includes both the medial and lateral condylar sliding surfaces. The medial condyle of the femoral component and the medial bearing shell of the meniscus part are also designed to be spherical. The meniscus part thus includes three sliding surfaces—medial condyle, lateral condyle and the surface of the tibia part/bottom side of the meniscus part.

It has been found in practice that the anatomical and kinematic relationships may be reproduced relatively well in knee endoprostheses of this design but they have increased abrasion of material when opposing stationary meniscus parts, wherein the sliding surfaces are not optimally coordinated with one another from the standpoint of material technology and there is therefore an increased risk of loosening of the implant.

The invention is based on the object of designing a knee endoprosthesis, so that it has the least possible abrasion with optimal reproduction of the anatomical and kinematic properties of the natural knee joint, in particular through suitable combinations of materials and a reduction in the abrasion-generating surfaces.

According to the invention, this object is achieved by the fact that the entire femoral component, but at least its condylar surfaces, consist of a solidly sintered ceramic for articulation with the tibial component, such that the tibial component comprises a tibial baseplate made of a solidly sintered ceramic, which has a medial spherical bearing shell on its surface facing the femoral component, wherein the medial spherical bearing shell is an integral component of the tibial baseplate and is designed in one piece with it, and the articulation surface of the medial femur condyle is also designed to be spherical and forms a congruent spherical joint together with the medial spherical bearing shell, and laterally next to the medial spherical bearing shell is arranged a bearing shell, which is formed from multiple radii in the anterior-posterior direction, enabling rotation of the femoral component and is arranged non-congruently with the femur condyle, either being designed in one piece with the tibial baseplate or being an inlay that is movable relative to the tibial baseplate. In this way, reduction in the abrasion-generating surfaces results in the least possible abrasion.

The tibial baseplate preferably has a bolt for anchoring on its bottom side facing the proximal tibia. The bolt is advantageously made of a solidly sintered ceramic and is formed in one piece with the tibial baseplate. The bolt may have a non-circular cross section and is thus anchored in the natural tibia in a rotationally fixed manner.

The inlay is preferably made of UHMWPE, PEEK, PAEK or composites of a solidly sintered ceramic or polyethylenes.

The inlay may be movable in a groove on the tibial baseplate, thereby enabling rotation of the femoral component. The groove is advantageously designed in a straight line in the anterior-posterior direction or with a radius of curvature that determines the femur rotation.

The femur rotation is preferably limited to max. 15° internal and external rotation.

For stabilization of the joint in extension (extended position), the bearing shell or the inlay preferably has an elevation in the anterior direction.

The condylar surface 1b, which is articulated in the bearing shell, advantageously also has a translational movement in the anterior-posterior direction in addition to the flexion movement.

A tibial component of a knee endoprosthesis according to the invention is characterized in that the tibial component comprises a tibial baseplate made of a solidly sintered ceramic, which has a medial spherical bearing shell as an integral component of the tibial baseplate, designed in one piece with it, and next to the media spherical bearing shell is arranged a bearing shell which enables rotation of the femoral component, is formed from several radii in the anterior-posterior direction and is arranged non-congruently with the femur condyle, being designed either in one piece with the tibial baseplate or being an inlay that is movable relative to the tibial baseplate.

The invention thus relates to a knee endoprosthesis comprising a tibia part, a femur part having two condylar surfaces and only one meniscus part, which is arranged exclusively between the lateral femur condyle and the tibia part and has on its upper face a bearing shell to receive and support the lateral condylar surfaces of the femur part and has on its bottom side an anchoring mechanism for fixed but releasable connection to the tibia part, wherein the medial bearing shell is an integral component of the tibial baseplate and the bearing shell has a spherical geometry and together with the spherical geometry of the medial femur condyle represents a congruent ball joint, wherein the tibia part forms a joint component (mono-block) with the medial bearing shell and is preferably made of a ceramic material and articulates with the femur part, which is also made of ceramic. The modular lateral meniscus part—fixed or mobile—is preferably made of UHMWPE and also articulates with the ceramic femur condyle.

Due to the fact that the medial bearing shell is designed to be spherical and is an integral component of the ceramic tibial baseplate, this medial ball joint offers the greatest possible congruence due to a ceramic/ceramic sliding pairing comparable to the ceramic/ceramic articulation in the hip endoprosthesis and promises minimal abrasion. Laterally, a bearing shell of an inlay that is to be connected to the ceramic tibia part or is movable relative to the tibia part ensures kinematics largely comparable to that of the natural joint, wherein said bearing shell is not congruent with the femur condyle, while enabling rotation of the femur component, wherein the inlay is manufactured from UHMWPE, PEEK, PAEK, composites of various materials such as ceramics/polyethylenes.

FIG. 1 shows a knee joint endoprosthesis according to the invention, which has a femur part with a femoral component 1 and comprises two condylar surfaces 1a, 1b, for anchoring on the distal femur and a tibial component 2 for anchoring on the proximal tibia. The tibial component consists of a tibial baseplate on whose lower side facing the tibia is arranged a bolt 6 for anchoring. According to the invention, a medial bearing shell 7, as an integral component of the ceramic tibial baseplate, is arranged on the upper face, i.e., on the side of the tibial baseplate facing the femoral component 1. This medial bearing shell 7 is designed to be spherical. Both the femoral component 1 and the tibial component 2 are manufactured from a solidly sintered ceramic, i.e., they are ceramic parts. This creates a ceramic/ceramic friction pairing, which has almost no abrasion even with prolonged use. Laterally a bearing shell 8 which enables rotation of the femur component, is formed from several radii in the anterior-posterior direction and is thus not concurrent with the femur condyle is arranged next to the medial bearing shell 7. This bearing shell 8 may be a bearing shell permanently connected to the tibial component 2 or an inlay that is movable relative to the tibial component 2 and has kinematics largely comparable to that of the natural joint. The movable inlay is preferably made of UHMWPE, PEEK, PAEK or composites of materials such as ceramics or polyethylenes.

Figure 2:
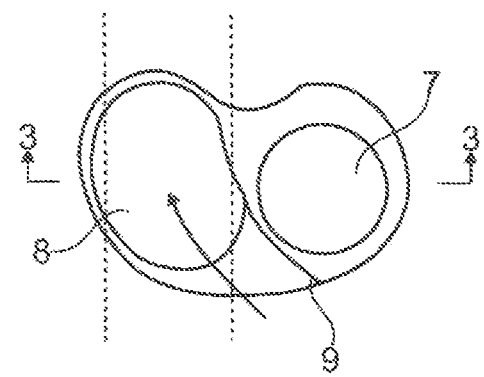

FIG. 1 shows an embodiment of a bearing shell 8, which is movable in a groove 9 in the tibial component 2. This groove 9 may be designed to be in a straight line in the anterior-posterior direction as shown by the dotted lines in FIG. 2 or also designed to have a radius of curvature that determines the femur rotation as shown in FIGS. 1 and 2, such that the femur rotation is limited to approx. 15° of internal and external rotation (not shown). The radius of curvature varies as a function of the respective size of the femur component.

FIG. 2 shows the tibial component 2 according to FIG. 1 in an overhead view of the tibial baseplate, facing the femoral component 1. This shows clearly the medial bearing shell 7, which is designed to be spherical. The bearing shell 8 which is not congruent with the femur condyle and may be permanently connected to the tibial baseplate (not shown) or designed to be movable in the groove 9 on the tibial baseplate is arranged next to the medial bearing shell 7.

Figure 3:
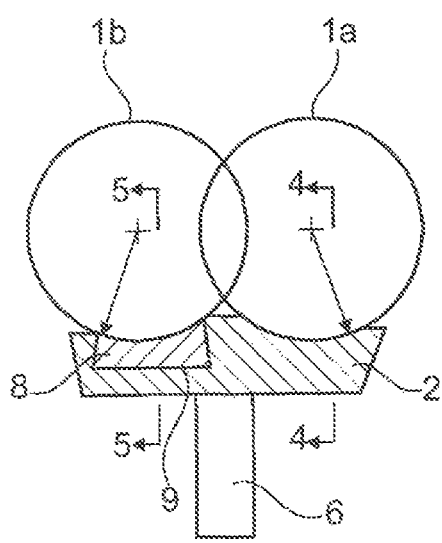

FIG. 3 shows a section along line 3-3 in FIG. 2. The bearing shell 8 which is not congruent with the femur condyle 1b in the anterior-posterior direction is permanently anchored on the tibial baseplate or is inserted movably into a groove 9 while the condylar surface 1a articulates congruently in the spherical medial bearing shell 7.

Figure 4:
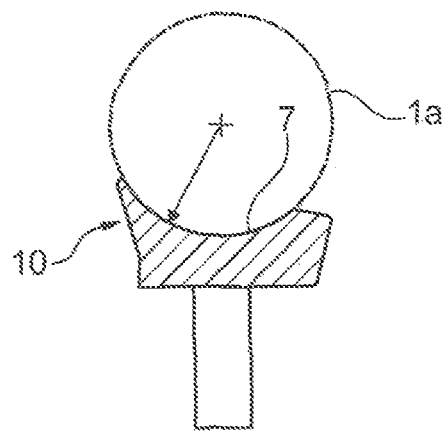

FIG. 4 shows a section along line 4-4 in FIG. 3. The condylar surface 1a articulates congruently in the spherical medial bearing shell 7. For stabilization of the joint in extension (extended position), the bearing shell 7 has an elevation 10 in the anterior direction.

Figure 5:
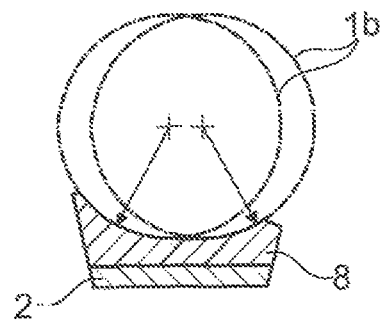

FIG. 5 shows a section along line 5-5 in FIG. 3. The condylar surface 1b articulates in the bearing shell 8 and permits a translational movement in the anterior-posterior direction in addition to the flexion movement. FIG. 5 shows two possible positions as well as the translational path of the condylar surface 1b.

LIST OF REFERENCE NUMERALS

1 Femoral component
1a Condylar surfaces
2 Tibial component
3 Line 3-3
4 Line 4-4
5 Line 5-5
6 Bolt
7 Medial bearing shell
8 Congruent bearing shell
9 Groove
10 Elevation
11 Tibial baseplate

The invention claimed is:

1. A knee endoprosthesis comprising:
a femoral component for anchoring on a distal femur, the femoral component having two condylar surfaces including a medial femoral condyle having a spherical articulation surface and a lateral femoral condyle; and
a tibial component for anchoring on a proximal tibia, the tibial component comprising:
a kidney-shaped tibial baseplate having a bone-engaging bottom surface and a stem protruding from said bottom surface, wherein the stem is sized and configured for anchoring in a medullary canal of the proximal tibia;
a medial spherical bearing shell in an upper surface of the tibial baseplate configured to face the femoral component, wherein the medial spherical bearing shell and the tibial baseplate are monolithically-formed, designed in one piece and made of a solidly sintered ceramic, wherein the spherical articulation surface of the medial femoral condyle and the medial spherical bearing shell together form a congruent ball joint; and
a lateral bearing shell provided on the tibial baseplate laterally next to the medial spherical bearing shell, which enables rotation of the femoral component, the lateral bearing shell being formed from several radii in the anterior-posterior direction and not being congruent with the lateral femoral condyle, the lateral bearing shell being an elongated and arcuate inlay that is movable relative to the tibial baseplate,
wherein the medial femoral condyle articulates with the medial spherical bearing shell, and the lateral femoral condyle articulates with the lateral bearing shell,
wherein at least the two condylar surfaces of the femoral component for articulation with the tibial component are made of a solidly sintered ceramic,
wherein the inlay is movable in a groove on the tibial baseplate.

2. The knee endoprosthesis according to claim 1, wherein the inlay is made of UHMWPE, PEEK, PAEK or composites or a solidly sintered ceramic or polyethylenes.

3. The knee endoprosthesis according to claim 1, wherein the groove is designed having a radius of curvature that determines femur rotation.

4. The knee endoprosthesis according to claim 3, wherein the femur rotation is limited to at most 15° of internal and external rotation.

5. The knee endoprosthesis according to claim 1, wherein the medial spherical bearing shell or the inlay has an elevation in the anterior direction.

* * * * *